(12) United States Patent
Decker et al.

(10) Patent No.: US 12,342,996 B2
(45) Date of Patent: Jul. 1, 2025

(54) THREE-DIMENSIONAL PRINTED SWABS FOR DIAGNOSTIC TESTING

(71) Applicants: University of South Florida, Tampa, FL (US); THE FEINSTEIN INSTITUTES FOR MEDICAL RESEARCH, Manhasset, NY (US)

(72) Inventors: Summer J. Decker, Apollo Beach, FL (US); Jonathan Ford, Tampa, FL (US); Todd Hazelton, Tampa, FL (US); Todd Goldstein, New Hyde Park, NY (US); Kami Kim, Tampa, FL (US); Michael Teng, Tampa, FL (US); John Sinnott, Tampa, FL (US)

(73) Assignees: University of South Florida, Tampa, FL (US); THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 705 days.

(21) Appl. No.: 17/178,867

(22) Filed: Feb. 18, 2021

(65) Prior Publication Data
US 2021/0290210 A1   Sep. 23, 2021

Related U.S. Application Data

(60) Provisional application No. 62/992,698, filed on Mar. 20, 2020.

(51) Int. Cl.
*A61B 10/02* (2006.01)
*A61B 10/00* (2006.01)
*B33Y 80/00* (2015.01)

(52) U.S. Cl.
CPC .......... *A61B 10/02* (2013.01); *A61B 10/0045* (2013.01); *B33Y 80/00* (2014.12); *A61B 2560/04* (2013.01)

(58) Field of Classification Search
CPC ............... G01N 2001/028; A61F 13/38; B01L 3/5029; A61B 10/02; A61B 10/0045
(Continued)

(56) References Cited

U.S. PATENT DOCUMENTS

| 4,027,658 A | 6/1977 | Marshall |
| 4,981,143 A | 1/1991 | Sakita et al. |

(Continued)

FOREIGN PATENT DOCUMENTS

| WO | 2010149366 A1 | 12/2010 |
| WO | 2012125757 A2 | 9/2012 |

OTHER PUBLICATIONS

International Search Report and Written Opinion issued for Application No. PCT/US2021/018510, dated May 5, 2021.
(Continued)

*Primary Examiner* — Charles A Marmor, II
(74) *Attorney, Agent, or Firm* — Meunier Carlin & Curfman LLC

(57) ABSTRACT

A three-dimensional printed swab may include a shaft defining a longitudinal axis of the swab, and a tip portion integrally formed with the shaft. The tip portion may include a plurality of protrusions each extending outward from the shaft and transverse to the longitudinal axis. A method for fabricating a three-dimensional printed swab may include receiving a digital three-dimensional model corresponding to the swab, and integrally forming, via three-dimensional printing and based at least in part on the digital three-dimensional model, a shaft and a tip portion of the swab. The shaft may define a longitudinal axis of the swab. The tip portion may include a plurality of protrusions each extending outward from the shaft and transverse to the longitudinal axis.

13 Claims, 6 Drawing Sheets

(58) Field of Classification Search
USPC .......................................................... D24/119
See application file for complete search history.

(56) References Cited

U.S. PATENT DOCUMENTS

| | | | |
|---|---|---|---|
| D379,508 S | | 5/1997 | Hudson et al. |
| D401,326 S | | 11/1998 | Powell et al. |
| D541,931 S | | 5/2007 | Tsaur |
| D545,430 S | | 6/2007 | Tsaur |
| D584,813 S | | 1/2009 | Watanabe |
| D585,998 S | | 2/2009 | Anderson |
| D614,292 S | | 4/2010 | Anderson |
| D628,708 S | | 12/2010 | Anderson |
| D631,957 S | * | 2/2011 | Perez .................... A61F 11/006 |
| | | | D24/119 |
| D701,600 S | | 3/2014 | Kauffman |
| 9,072,499 B2 | | 7/2015 | Birnboim et al. |
| 9,233,027 B1 | | 1/2016 | Jackson |
| D772,398 S | | 11/2016 | Triva |
| D779,654 S | | 2/2017 | Pourbaba |
| D800,981 S | | 10/2017 | Pisacane et al. |
| D914,203 S | | 3/2021 | Aagaard et al. |
| D945,603 S | * | 3/2022 | Frandsen ..................... D24/119 |
| D946,751 S | | 3/2022 | Ebel |
| D956,962 S | | 7/2022 | Lyon |
| D965,771 S | | 10/2022 | Lund et al. |
| D970,000 S | | 11/2022 | James |
| D972,130 S | | 12/2022 | Decker et al. |
| D975,270 S | | 1/2023 | Browka |
| D977,089 S | | 1/2023 | Ozdoganlar et al. |
| D977,090 S | | 1/2023 | Ozdoganlar et al. |
| D977,091 S | | 1/2023 | Ozdoganlar et al. |
| D982,158 S | | 3/2023 | Yeom et al. |
| 2010/0069791 A1 | | 3/2010 | Ernster |
| 2011/0179887 A1 | | 7/2011 | Cobian et al. |
| 2012/0192892 A1 | | 8/2012 | Kulik |
| 2012/0271196 A1 | | 10/2012 | Triva |
| 2013/0304103 A1 | | 11/2013 | Burres |
| 2014/0277659 A1 | | 9/2014 | Kumar et al. |
| 2015/0018861 A1 | | 1/2015 | Olson |
| 2017/0049422 A1 | | 2/2017 | Ferris |
| 2020/0060877 A1 | * | 2/2020 | Belmkaddem ........ A61F 11/006 |
| 2021/0290210 A1 | | 9/2021 | Decker et al. |
| 2021/0321991 A1 | * | 10/2021 | Elliott .................... A61B 10/02 |

OTHER PUBLICATIONS

Non-Final Office Action issued in connection with U.S. Appl. No. 17/178,816, mailed May 26, 2023.
Ford, Jonathan, "A 3D-printed nasopharyngeal swab for COVID-19 diagnostic testing," 3D Printing in Medicine, vol. 6, No. 1, Aug. 15, 2020, 7 pages.
Extended European Search Report issued in EP Application No. 21771379.1, on Mar. 13, 2024, 16 pages.

* cited by examiner

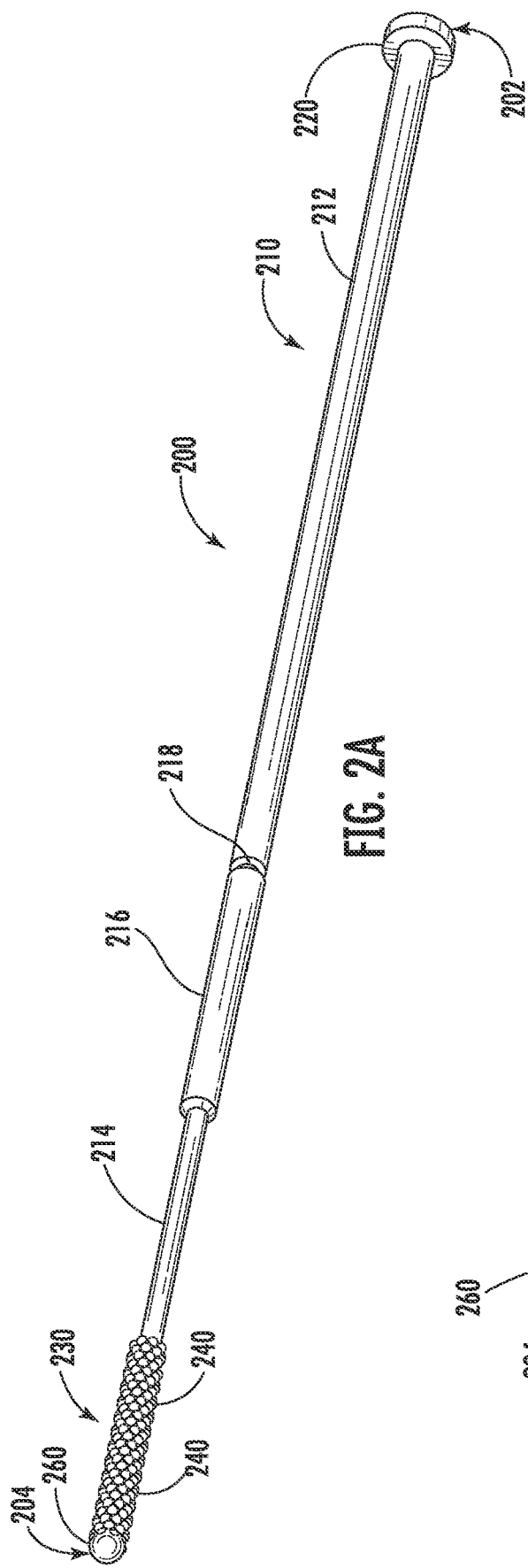
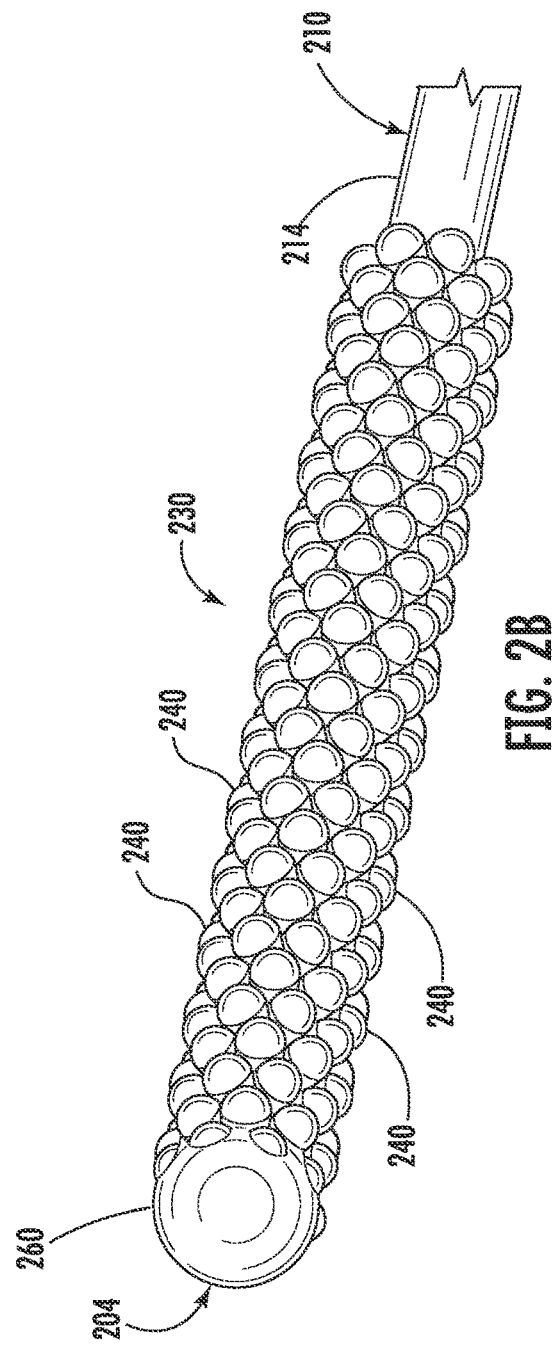
FIG. 2A
FIG. 2B

THREE-DIMENSIONAL PRINTED SWABS FOR DIAGNOSTIC TESTING

CROSS-REFERENCE TO RELATED APPLICATIONS

This application claims priority to and the benefit of U.S. Provisional Patent Application No. 62/992,698, filed on Mar. 20, 2020, the disclosure of which is expressly incorporated herein by reference in its entirety.

FIELD OF THE DISCLOSURE

The present disclosure relates generally to swabs used for sample collection and more particularly to three-dimensional printed swabs used to collect biological samples for diagnostic testing.

BACKGROUND OF THE DISCLOSURE

Various types of devices may be used to collect biological samples for diagnostic testing. In many instances, swabs having a shaft and a tip portion may be used for sample collection. During use, the shaft may be grasped and manipulated by a user to advance the tip portion to a target location of a subject and collect a sample therefrom. For example, a tip portion of a nasopharyngeal swab may be advanced through a subject's nostril to collect a sample from the surface of the respiratory mucosa for evaluating a suspected viral infection. For different diagnostic tests, various other types of swabs may be configured for insertion into other anatomical sites of a subject to reach different target locations and collect samples therefrom.

Existing swabs typically may be formed of two or more materials. The shaft may be formed of a first material, and the tip portion may be formed of a different, second material and attached to the shaft. For example, traditional swabs may have a wooden shaft and a cotton tip portion. Other swabs may have a shaft formed of a suitable plastic and a flocked tip portion formed of a suitable synthetic material, such as nylon. Swabs often may be provided as a part of a test kit that also includes a vessel for containing the swab after sample collection and media for facilitating transport of the sample. For example, universal viral diagnostic test kits typically may include a minitip flocked swab and a test tube containing viral transport media. Importantly, traditional swabs formed of wood and cotton often may not be suitable due to reactions between testing chemicals and the swab materials.

The fabrication and use of existing swabs may present certain limitations. For example, during a period of increased demand for swabs, as may result from a pandemic disease, manufacturing capacity and/or a supply of material may not be sufficient to meet the demand. Additionally, for swabs having a shaft and a tip portion formed of different materials, manufacturing lead times may be impacted by the time required to attach the tip material to the shaft material. Further, the tip portions of existing swabs may not be suitable or preferable for collecting biological samples for certain diagnostic testing applications.

A need therefore exists for improved swabs for use in collecting biological samples for diagnostic testing and related methods for fabricating such swabs, which may overcome one or more of the above-mentioned limitations associated with existing swabs and their fabrication.

SUMMARY OF THE DISCLOSURE

The present disclosure provides three-dimensional printed swabs and related methods for fabricating three-dimensional printed swabs. In one aspect, a three-dimensional printed swab is provided. In one embodiment, the three-dimensional printed swab may include a shaft defining a longitudinal axis of the swab, and a tip portion integrally formed with the shaft. The tip portion may include a plurality of protrusions each extending outward from the shaft and transverse to the longitudinal axis.

In some embodiments, the plurality of protrusions may include a series of circumferential arrays of protrusions positioned along the longitudinal axis. In some embodiments, each of the circumferential arrays of protrusions may include four or more protrusions having respective free ends equally spaced apart from one another in a circumferential direction around the longitudinal axis. In some embodiments, the four or more protrusions may have respective base ends equally spaced apart from one another in the circumferential direction. In some embodiments, consecutive pairs of the four or more protrusions may have respective base ends positioned adjacent one another in the circumferential direction. In some embodiments, the series of circumferential arrays of protrusions may include a first circumferential array of protrusions and a second circumferential array of protrusions positioned consecutively along the longitudinal axis, and the protrusions of the first circumferential array of protrusions may be offset from the protrusions of the second circumferential array of protrusions in the circumferential direction. In some embodiments, the series of circumferential arrays of protrusions also may include a third circumferential array of protrusions positioned consecutively along the longitudinal axis with respect to the second circumferential array of protrusions, and the protrusions of the first circumferential array of protrusions may be aligned with the protrusions of the third circumferential array of protrusions in the circumferential direction. In some embodiments, the circumferential arrays of protrusions may be equally spaced apart from one another along the longitudinal axis. In some embodiments, consecutive pairs of the circumferential arrays of protrusions may be positioned adjacent one another along the longitudinal axis.

In some embodiments, each of the protrusions may extend perpendicular to the longitudinal axis. In some embodiments, each of the protrusions may include a protrusion base extending from the shaft and having a cylindrical shape, and a protrusion tip extending from the protrusion base and having a partial-spherical shape. In some embodiments, the tip portion also may include a tip defining a distal end of the swab and having a partial-spherical shape. In some embodiments, the shaft may have a circular cross-sectional shape, and the shaft may include a proximal portion and a distal portion. The proximal portion may have a first diameter, and the distal portion may have a second diameter that is less than the first diameter. The protrusions may extend outward from the distal portion, and free ends of the protrusions may define a third diameter that is greater than the first diameter. In some embodiments, the shaft also may include an intermediate portion and a separation portion. The intermediate portion may be positioned between the proximal portion and the distal portion and may have the first diameter. The separation portion may be positioned between the proximal portion and the intermediate portion and may have the second diameter. The separation portion may be configured to facilitate separation of the proximal portion from the intermediate portion. In some embodiments, the shaft and the tip portion may be formed of the same material.

In another aspect, a three-dimensional printed swab is provided. In one embodiment, the three-dimensional printed swab may include a shaft defining a longitudinal axis of the swab and having a circular cross-sectional shape, and a tip portion integrally formed with the shaft. The shaft may include a proximal portion having a first diameter, and a distal portion having a second diameter that is less than the first diameter. The tip portion may include a plurality of protrusions each extending outward from the shaft and transverse to the longitudinal axis, and a tip defining a distal end of the swab and having a partial spherical shape. Free ends of the protrusions may define a third diameter that is greater than the first diameter. The tip may have a fourth diameter that is less than the third diameter and greater than the first diameter.

In some embodiments, the plurality of protrusions may include a series of circumferential arrays of protrusions positioned along the longitudinal axis, and each of the circumferential arrays of protrusions may include four or more protrusions having respective free ends equally spaced apart from one another in a circumferential direction around the longitudinal axis. In some embodiments, the shaft and the tip portion may be formed of the same material.

In still another aspect, a method for fabricating a three-dimensional printed swab. In one embodiment, the method may include receiving a digital three-dimensional model corresponding to the swab, and integrally forming, via three-dimensional printing and based at least in part on the digital three-dimensional model, a shaft and a tip portion of the swab. The shaft may define a longitudinal axis of the swab, and the tip portion may include a plurality of protrusions each extending outward from the shaft and transverse to the longitudinal axis.

In some embodiments, the plurality of protrusions may include a series of circumferential arrays of protrusions positioned along the longitudinal axis, and each of the circumferential arrays of protrusions may include four or more protrusions having respective free ends equally spaced apart from one another in a circumferential direction around the longitudinal axis. In some embodiments, the shaft and the tip portion may be formed of the same material.

These and other aspects and improvements of the present disclosure will become apparent to one of ordinary skill in the art upon review of the following detailed description when taken in conjunction with the several drawings and the appended claims.

BRIEF DESCRIPTION OF THE DRAWINGS

FIG. 2A is a perspective view of an example three-dimensional printed swab in accordance with one or more embodiments of the disclosure, the swab including a shaft and a tip portion.

FIG. 2B is a detailed perspective view of the tip portion of the three-dimensional printed swab of FIG. 2A.

Figure 1A:
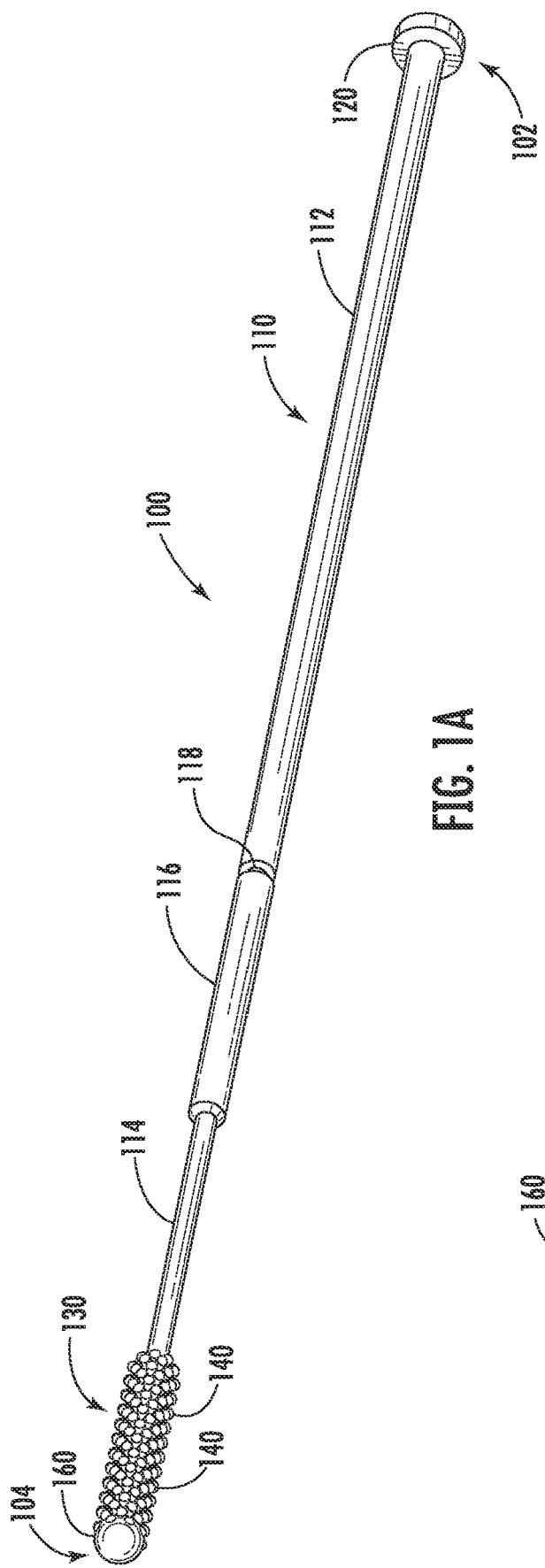
FIG. 1A is a perspective view of an example three-dimensional printed swab in accordance with one or more embodiments of the disclosure, the swab including a shaft and a tip portion.
Figure 1B:
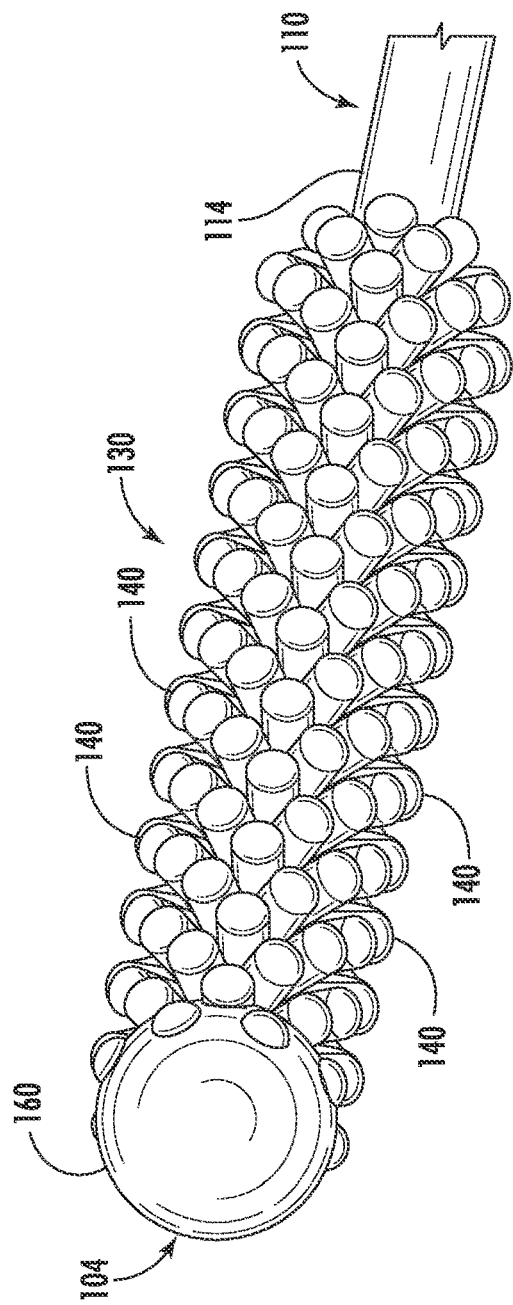
FIG. 1B is a detailed perspective view of the tip portion of the three-dimensional printed swab of FIG. 1A.
Figure 1C:
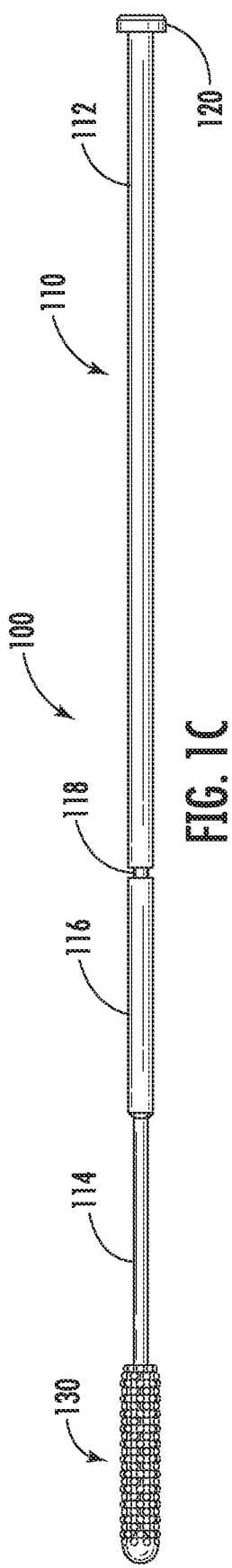
FIG. 1C is a front view of the three-dimensional printed swab of FIG. 1A.
Figure 1D:
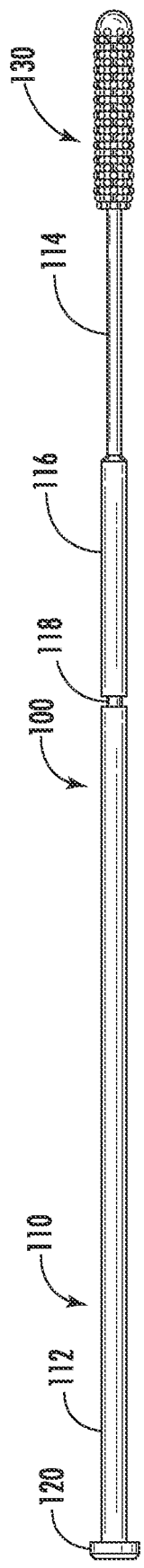
FIG. 1D is a rear view of the three-dimensional printed swab of FIG. 1A.
Figure 1E:
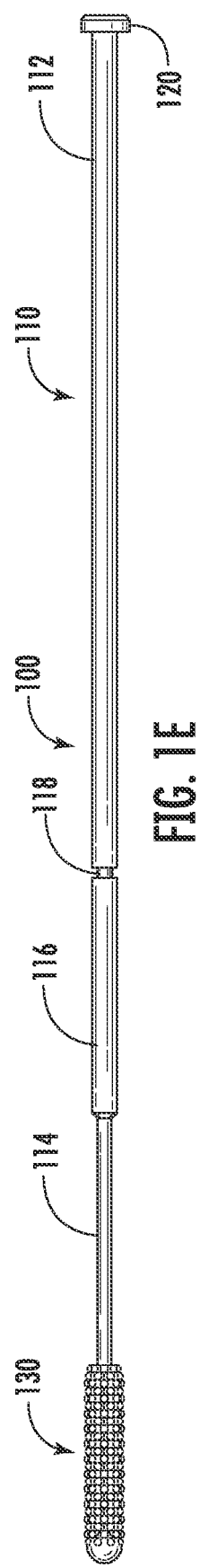
FIG. 1E is a top view of the three-dimensional printed swab of FIG. 1A.
Figure 1F:
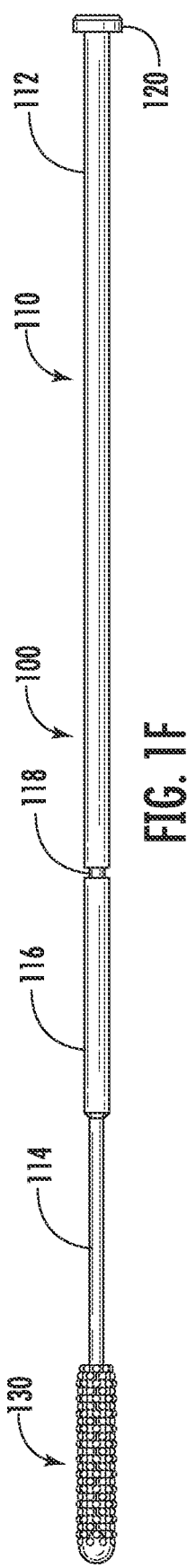
FIG. 1F is a bottom view of the three-dimensional printed swab of FIG. 1A.
Figure 1H:
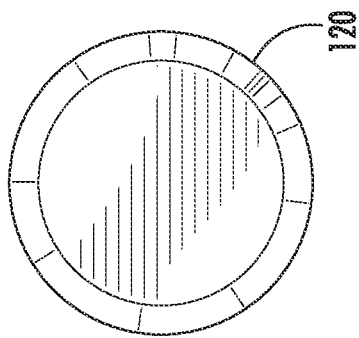
FIG. 1H is a detailed right-end view of the three-dimensional printed swab of FIG. 1A.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

Embodiments of three-dimensional printed swabs and related methods for fabricating three-dimensional printed swabs are provided herein. The three-dimensional printed swabs may be used to collect biological samples from a subject, such as a human subject, for diagnostic testing. For example, the three-dimensional printed swabs may be configured for use as a nasopharyngeal swab to be advanced through a subject's nostril to collect a sample from the surface of the respiratory mucosa for evaluating a suspected viral infection. Various other configurations of the three-dimensional printed swabs may be implemented for accommodating insertion into other anatomical sites of a subject to reach different target locations and collect samples therefrom. In some embodiments, the three-dimensional printed swabs may be provided as a part of a test kit that also includes a vessel for containing the swab or a portion of the swab after sample collection and media for facilitating transport of the sample. For example, the three-dimensional printed swabs may be provided as a part of a universal viral diagnostic test kit that also includes a test tube containing viral transport media.

The three-dimensional printed swabs provided herein generally may include a shaft defining a longitudinal axis of the swab, and a tip portion integrally formed with the shaft. The tip portion may include a plurality of protrusions each extending outward from the shaft and transverse to the longitudinal axis. The methods for fabricating a three-dimensional printed swab provided herein generally may include receiving a digital three-dimensional model corresponding to the swab, and integrally forming, via three-dimensional printing and based at least in part on the digital three-dimensional model, a shaft and a tip portion of the swab. The shaft may define a longitudinal axis of the swab, and the tip portion may include a plurality of protrusions each extending outward from the shaft and transverse to the longitudinal axis.

As discussed above, existing swabs for collecting biological samples for diagnostic testing and existing techniques for fabricating such swabs may have certain limitations. In some instances, during a period of increased demand for swabs, as may result from a pandemic disease, manufacturing capacity and/or a supply of material for fabricating such swabs may not be sufficient to meet the demand. Moreover, for existing swabs having a shaft and a tip portion formed of different materials, manufacturing lead times may be adversely impacted by the time required to attach the tip material to the shaft material. Further, when considering certain diagnostic testing applications, the tip portions of existing swabs may not be suitable or preferable for collecting biological samples from the respective target locations.

The three-dimensional printed swabs and related methods for fabricating three-dimensional printed swabs provided herein advantageously may overcome one or more of the limitations associated with existing swabs and techniques for their fabrication. As described herein, the swabs may be fabricated by three-dimensional (3D) printing, a form of additive manufacturing. In particular, fabrication methods may include receiving a digital three-dimensional (3D) model corresponding to the swab, and integrally forming, via three-dimensional printing and based at least in part on the digital three-dimensional model, the shaft and the tip portion of the swab. In this manner, because three-dimensional printing may utilize different equipment and materials than those used for manufacture of existing swabs, fabrication of the swabs described herein may be unaffected by limited manufacturing capacity and/or a limited supply of material for existing swabs during a period of increased demand. The fabrication of the three-dimensional printed swabs may be carried out using any three-dimensional printers and any materials that are suitable for patient use (i.e., those cleared by the Food and Drug Administration (FDA) or other relevant regulatory authority for patient use). The digital three-dimensional model may be a Computer Aided Design (CAD) model created using various forms of 3D modeling software. Additionally, because the shaft and the tip portion of the three-dimensional printed swabs may be integrally formed with one another, fabrication of the swabs may avoid the need to separately attach the tip portion to the shaft, as is required for existing swabs. Further, in certain applications, the tip portion of the three-dimensional printed swabs may be configured to improve sample collection as compared to existing swabs. As described herein, the protrusions of the tip portion may be configured to facilitate collection of a biological sample thereon. In particular, the size, shape, number, and/or arrangement of the protrusions may be selected to maximize a surface area of the tip portion that is configured to contact a target location of a subject, thereby improving sample collection.

Still other benefits and advantages of the three-dimensional printed swabs and fabrication methods provided herein over existing swab technology will be appreciated by those of ordinary skill in the art from the following description and the appended drawings.

Example Embodiments of Swabs

Referring now to FIGS. 1A-1I, an example three-dimensional printed swab 100 (which also may be referred to as a "3D-printed swab," or simply a "swab") is depicted. The three-dimensional printed swab 100 is configured for collecting biological samples from a subject, such as a human subject, for diagnostic testing. The three-dimensional printed swab 100 may be particularly well suited for use with an adult human subject. In some embodiments, the three-dimensional printed swab 100 may be configured for use as a nasopharyngeal swab to be advanced through a subject's nostril to collect a sample from the surface of the respiratory mucosa for evaluating a suspected viral infection. Various other configurations of and uses for the three-dimensional printed swab 100 may be envisioned by those of ordinary skill in the art for accommodating insertion into other anatomical sites of a subject to reach different target locations and collect samples therefrom for different diagnostic tests.

As shown, the three-dimensional printed swab 100 may have an elongated, linear shape with a proximal end 102 (which also may be referred to as a "first end") and a distal end 104 (which also may be referred to as a "second end") positioned opposite one another along a longitudinal axis $A_L$ of the swab 100. In some embodiments, the swab 100, or at least a portion of the swab 100, may be flexible such that the swab 100 may be elastically deformed from its linear shape but has a tendency to return to its original, linear shape.

The three-dimensional printed swab 100 may include a shaft 110 and a tip portion 130 that is integrally formed with the shaft 110. During use of the swab 100, the shaft 110 may be grasped and manipulated by a user to advance the tip portion 130 to a target location of a subject and collect a sample therefrom. As described below, the tip portion 130 may be configured to facilitate collection of a biological sample thereon. As shown, the shaft 110 may define the longitudinal axis $A_L$ of the swab 100. In other words, a longitudinal axis of the shaft 110 may be coaxial with the longitudinal axis $A_L$ of the swab 100. Similarly, a longitudinal axis of the tip portion 130 may be coaxial with the longitudinal axis $A_L$ of the swab 100. As shown, the shaft 110 may extend from the proximal end 102 toward the distal end 104 of the swab 110, and the tip portion 130 may extend from the distal end 104 toward the proximal end 102 of the swab 100. In other words, a proximal end of the shaft 110 may define the proximal end 102 of the swab 110, and a distal end of the tip portion 130 may define the distal end 104 of the swab 110. In some embodiments, as shown, the shaft 110 and the tip portion 130 may be symmetric about the longitudinal axis $A_L$ of the swab 100. In some embodiments, the shaft 110 and/or the tip portion 130 may be asymmetric about the longitudinal axis $A_L$ of the swab 100. In some embodiments, the shaft 110 and the tip portion 130 may be formed of the same material. In some embodiments, the shaft 110, or at least a portion of the shaft 110, may be formed of a first material, and the tip portion 130, or at least a portion of the tip portion 130, may be formed of a second material that is different from the first material.

As shown, the shaft 110 may have a cylindrical shape and a circular cross-sectional shape (as viewed in a cross-section taken perpendicular to the longitudinal axis $A_L$ of the swab 100), although other shapes of the shaft 110 may be used in other embodiments. In some embodiments, the shaft 110 may include two or more portions having different diameters (or different maximum and/or minimum dimensions perpendicular to the longitudinal axis $A_L$ of the swab 100 in embodiments in which the cross-sectional shape of the shaft 110 is non-circular). For example, as shown, the shaft 110 may include a proximal portion 112 having a first diameter, and a distal portion 114 having a second diameter that is less than the first diameter. In some embodiments, the first diameter may be 2.5 mm, and the second diameter may be 1.5 mm, although other values of the first diameter and the second diameter may be used in other embodiments. The shaft 110 also may include an intermediate portion 116 and a separation portion 118. As shown, the intermediate portion 116 may be positioned between the proximal portion 112 and the distal portion 114 and may have a diameter that is equal to the first diameter of the proximal portion 112. In other embodiments, the diameter of the intermediate portion 116 may be greater than the first diameter of the proximal portion 112 or less than the first diameter of the proximal portion 112 but greater than the second diameter of the distal portion 114. As shown, the separation portion 118 may be positioned between the proximal portion 112 and the intermediate portion 116 and may have a diameter that is equal to the second diameter of the distal portion 114. In other embodiments, the diameter of the separation portion 118 may be less than the second diameter of the distal portion 114 or greater than the second diameter of the distal portion 114 but less than the first diameter of the proximal portion 112 and the intermediate portion 116. In some embodiments, each of the diameters of the proximal portion 112, the distal portion 114, the intermediate portion 116, and the separation portion 118 may be constant along the length of the respective portion. In some embodiments, one or more, or all, of the diameters of the proximal portion 112, the distal portion 114, the intermediate portion 116, and the separation portion 118 may vary along the length of the respective portion of the shaft 110. In such instances, the above-mentioned diameter of the respective portion having a varying diameter may be a maximum diameter of the respective portion of the shaft 110.

The separation portion 118 may be configured to facilitate separation of the proximal portion 112 from the intermediate portion 116. In particular, the smaller diameter of the separation portion 118 may allow a user to separate the proximal portion 112 from the intermediate portion 116 (and the remainder of the swab 100) upon grasping the proximal portion 112 and the intermediate portion 116 and apply bending forces thereto until the separation portion 118 breaks. In this manner, after using the swab 100 to collect a sample, the separation portion 118 may be broken, the distal portion 114, the intermediate portion 116, and the tip portion 130 may be inserted into a transport vessel, such as a test tube, and the proximal portion 112 may be discarded. In some embodiments, the shaft 110 also may include a flange 120 extending outward from the proximal portion 112. The flange 120 may be positioned at or near the proximal end 102 of the swab 100. In this manner, the flange 120 may be configured to facilitate grasping and manipulation of the swab 100 by a user. Upon breaking the separation portion 118 of the swab 100, the flange 120 would be discarded along with the proximal portion 112.

Figure 1G:
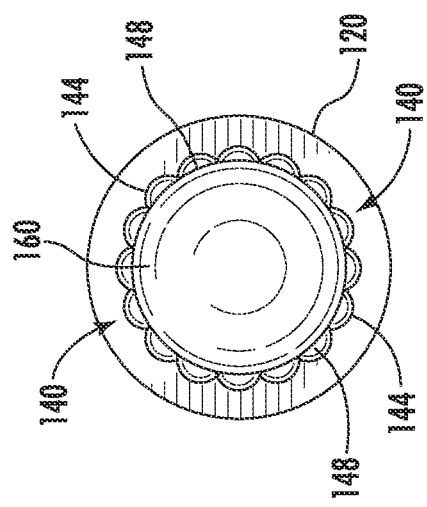
FIG. 1G is a detailed left-end view of the three-dimensional printed swab of FIG. 1A.
Figure 1I:
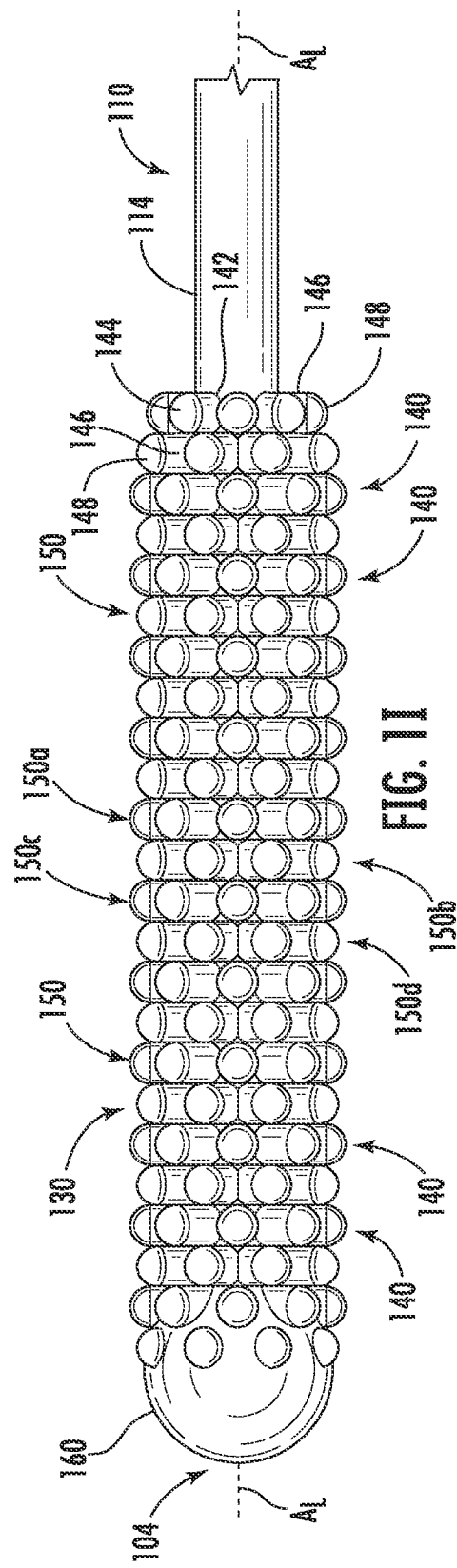
FIG. 1I is a detailed front view of the tip portion of the three-dimensional printed swab of FIG. 1A.

As shown, the tip portion 130 may include a plurality of protrusions 140 each extending outward from the shaft 110 and transverse to the longitudinal axis Ar of the swab 100. The protrusions 140 may be configured to facilitate collection of a biological sample thereon. In some embodiments, as shown, the protrusions 140 may extend outward from the distal portion 114 of the shaft 110. In some embodiments, as shown, each of the protrusions 140 may extend perpendicular to the longitudinal axis $A_L$ of the swab 100. In other words, each of the protrusions 140 may extend in a radial direction relative to the longitudinal axis $A_L$ of the swab 100. Each of the protrusions 140 may have a base end 142 and a free end 144, with a distance between the base end 142 and the free end 144 defining a height (which alternatively may be referred to as a "length") of the protrusion 140. The free ends 144 may define a third diameter, as shown in FIG. 1G. In some embodiments, as shown, the third diameter may be greater than the first diameter of the proximal portion 112 and thus also greater than the second diameter of the distal portion 114.

As shown, each of the protrusions 140 may include a protrusion base 146 and a protrusion tip 148. The protrusion base 146 may extend from the base end 142 to the protrusion tip 148, and the protrusion tip 148 may extend from the protrusion base 146 to the free end 144. In some embodiments, as shown, the protrusion base 146 may have a cylindrical shape, and the protrusion tip 148 may have a partial-spherical shape, such as a hemispherical same. Other shapes of the protrusion base 146 and the protrusion tip 148 may be used in other embodiments. In some embodiments, all of the protrusions 140 may have the same shape and the same size. In other embodiments, some of the protrusions 140 may have the same shape and the same size, while other protrusions 140 may have a different shape and/or a different size. For example, as shown in the illustrated embodiment, some of the protrusions 140 positioned at or near the proximal end or the distal end of the tip portion 130 may be smaller than the protrusions 140 positioned along an intermediate section of the tip portion 130 and/or may not include a cylindrical base.

As shown, the plurality of protrusions 140 may include a series of circumferential arrays 150 of the protrusions 140 positioned along the longitudinal axis $A_L$ of the swab 100. In some embodiments, the plurality of protrusions 140 may include four (4) or more circumferential arrays 150 positioned in series. Although twenty-four (24) circumferential arrays 150 of the protrusions 140 are provided in the illustrated embodiment, fewer or more circumferential arrays 150 positioned in series may be used in other embodiments. In some embodiments, each of the circumferential arrays 150 may include four (4) or more protrusions 140 positioned in an array. Although eight (8) protrusions 140 are provided for each of the circumferential arrays 150 in the illustrated embodiment, fewer or more protrusions 140 for each of the circumferential arrays 150 may be used in other embodiments. In some embodiments, as shown, for each of the circumferential arrays 150, the respective free ends 144 of the protrusions 140 of the circumferential array 150 may be equally spaced apart from one another in the circumferential direction around the longitudinal axis $A_L$ of the swab 100. In some embodiments, for each of the circumferential arrays 150, the respective free ends 144 of the protrusions 140 of the circumferential array 150 may be spaced apart from one another at unequal distances in the circumferential direction. In some embodiments, as shown, for each or some of the circumferential arrays 150, the respective base ends 142 of consecutive pairs of the protrusions 140 of the circumferential array 150 may be positioned adjacent one another in the circumferential direction. In other words, the respective base ends 142 of consecutive pairs of the protrusions 140 may not be spaced apart from one another. In some embodiments, for each or some of the circumferential arrays 150, the respective base ends 142 of the protrusions 140 of the circumferential array 150 may be equally spaced apart from one another in the circumferential direction. In some embodiments, for each or some of the circumferential arrays 150, the respective base ends 142 of the protrusions 140 of the circumferential array 150 may be spaced apart from one another at unequal distances in the circumferential direction.

As shown, the series of circumferential arrays 150 of the protrusions 140 may include a first circumferential array 150a, a second circumferential array 150b, a third circumferential array 150c, and a fourth circumferential array 150d positioned consecutively along the longitudinal axis $A_L$ of the swab 100. In some embodiments, the respective protrusions 140 of each consecutive pair of circumferential arrays 150 may be offset from one another in the circumferential direction. For example, as shown, the protrusions 140 of the first circumferential array 150a may be offset from the protrusions 140 of the second circumferential array 150b in the circumferential direction, the protrusions 140 of the second circumferential array 150b may be offset from the protrusions 140 of the third circumferential array 150c in the circumferential direction, and the protrusions 140 of the third circumferential array 150c may be offset from the protrusions 140 of the fourth circumferential array 150d in the circumferential direction. In some embodiments, the respective protrusions 140 of each pair of circumferential arrays 150 separated from one another by only a single other circumferential array 150 may be aligned with one another in the circumferential direction. For example, as shown, the protrusions 140 of the first circumferential array 150a may be aligned with the protrusions 140 of the third circumferential array 150c in the circumferential direction, and the protrusions 140 of the second circumferential array 150b may be aligned with the protrusions 140 of the fourth circumferential array 150d in the circumferential direction.

In some embodiments, as shown, respective consecutive pairs of the circumferential arrays 150 may be positioned adjacent one another along the longitudinal axis $A_L$ of the swab 100. In other words, the respective base ends 142 of the protrusions 140 of consecutive pairs of the circumferential arrays 150 may not be spaced apart from one another along the longitudinal axis $A_L$ of the swab 100. In some embodiments, the circumferential arrays 150 may be positioned equally spaced apart from one another along the longitudinal axis $A_L$ of the swab 100. In some embodiments, the circumferential arrays 150 may be spaced apart from one another at unequal distances along the longitudinal axis $A_L$ of the swab 100. Various configurations of the series of circumferential arrays 150 may be used in different embodiments.

In some embodiments, the tip portion 130 also may include tip 160. As shown, the tip 160 may be positioned at the distal end of the tip portion 130 and may define the distal end 104 of the swab 100. The tip 160 may be configured to contact anatomical features and to guide the tip portion 130 to a target location of a subject during use of the swab 100. As shown, the tip 160 may include a rounded or otherwise curved surface for atraumatically contacting anatomical features of the subject. In some embodiments, as shown, the tip 160 may have a partial-spherical shape, although other shapes for the tip 160 may be used in other embodiments. In some embodiments, as shown, the protrusions 140 of one or more of the circumferential arrays 150 may extend outward from a portion of the tip 160, such as from a proximal half of the tip 160, while a distal half of the tip 160 may be devoid of any protrusions 140 extending therefrom. In some embodiments, the entire tip 160 may be devoid of any protrusions 140 extending therefrom. The tip 160 may have a fourth diameter, as shown in FIG. 1G. In some embodiments, as shown, the fourth diameter of the tip 160 may be less than the third diameter defined by the free ends 144 of the protrusions 140, greater than the first diameter of the proximal portion 112, and thus also greater than the second diameter of the distal portion 114.

In some embodiments, the respective features of the three-dimensional printed swab 100 may have the relative dimensional relationships depicted in FIGS. 1A-1I. Such relative dimensional relationships may make the three-dimensional printed swab 100 particularly well suited for collecting biological samples from an adult human subject for diagnostic testing. Various other suitable relative dimensional relationships between respective features of the three-dimensional printed swab 100 may be used in other embodiments.

FIGS. 2A-2I depict another example three-dimensional printed swab 200 (which also may be referred to as a "3D-printed swab," or simply a "swab"). Certain similarities and differences between the three-dimensional printed swab 200 and the three-dimensional printed swab 100 described above will be appreciated from the drawings and the following description. Corresponding reference numbers are used for corresponding features, which generally may be configured in a manner similar to the features described above unless indicated otherwise. The three-dimensional printed swab 200 is configured for collecting biological samples from a subject, such as a human subject, for diagnostic testing. The three-dimensional printed swab 200 may be particularly well suited for use with a pediatric human subject. In some embodiments, the three-dimensional printed swab 200 may be configured for use as a nasopharyngeal swab to be advanced through a subject's nostril to collect a sample from the surface of the respiratory mucosa for evaluating a suspected viral infection. Various other configurations of and uses for the three-dimensional printed swab 200 may be envisioned by those of ordinary skill in the art for accommodating insertion into other anatomical sites of a subject to reach different target locations and collect samples therefrom for different diagnostic tests.

As shown, the three-dimensional printed swab 200 may have an elongated, linear shape with a proximal end 202 (which also may be referred to as a "first end") and a distal end 204 (which also may be referred to as a "second end") positioned opposite one another along a longitudinal axis $A_L$ of the swab 200. In some embodiments, the swab 200, or at least a portion of the swab 200, may be flexible such that the swab 200 may be elastically deformed from its linear shape but has a tendency to return to its original, linear shape.

The three-dimensional printed swab 200 may include a shaft 210 and a tip portion 230 that is integrally formed with the shaft 210. During use of the swab 200, the shaft 210 may be grasped and manipulated by a user to advance the tip portion 230 to a target location of a subject and collect a sample therefrom. As described below, the tip portion 230 may be configured to facilitate collection of a biological sample thereon. As shown, the shaft 210 may define the longitudinal axis $A_L$ of the swab 200. In other words, a longitudinal axis of the shaft 210 may be coaxial with the longitudinal axis $A_L$ of the swab 200. Similarly, a longitudinal axis of the tip portion 230 may be coaxial with the longitudinal axis $A_L$ of the swab 200. As shown, the shaft 210 may extend from the proximal end 202 toward the distal end 204 of the swab 200, and the tip portion 230 may extend from the distal end 204 toward the proximal end 202 of the swab 200. In other words, a proximal end of the shaft 210 may define the proximal end 202 of the swab 210, and a distal end of the tip portion 230 may define the distal end 204 of the swab 210. In some embodiments, as shown, the shaft 210 and the tip portion 230 may be symmetric about the longitudinal axis $A_L$ of the swab 200. In some embodiments, the shaft 210 and/or the tip portion 230 may be asymmetric about the longitudinal axis $A_L$ of the swab 200. In some embodiments, the shaft 210 and the tip portion 230 may be formed of the same material. In some embodiments, the shaft 210, or at least a portion of the shaft 210, may be formed of a first material, and the tip portion 230, or at least a portion of the tip portion 230, may be formed of a second material that is different from the first material.

As shown, the shaft 210 may have a cylindrical shape and a circular cross-sectional shape (as viewed in a cross-section taken perpendicular to the longitudinal axis $A_L$ of the swab 200), although other shapes of the shaft 210 may be used in other embodiments. In some embodiments, the shaft 210 may include two or more portions having different diameters (or different maximum and/or minimum dimensions perpendicular to the longitudinal axis $A_L$ of the swab 200 in embodiments in which the cross-sectional shape of the shaft 210 is non-circular). For example, as shown, the shaft 210 may include a proximal portion 212 having a first diameter, and a distal portion 214 having a second diameter that is less than the first diameter. In some embodiments, the first diameter may be 2.5 mm, and the second diameter may be 1.5 mm, although other values of the first diameter and the second diameter may be used in other embodiments. The shaft 210 also may include an intermediate portion 216 and a separation portion 218. As shown, the intermediate portion 216 may be positioned between the proximal portion 212 and the distal portion 214 and may have a diameter that is equal to the first diameter of the proximal portion 212. In other embodiments, the diameter of the intermediate portion 216 may be greater than the first diameter of the proximal portion 212 or less than the first diameter of the proximal portion 212 but greater than the second diameter of the distal portion 214. As shown, the separation portion 218 may be positioned between the proximal portion 212 and the intermediate portion 216 and may have a diameter that is equal to the second diameter of the distal portion 214. In other embodiments, the diameter of the separation portion 218 may be less than the second diameter of the distal portion 214 or greater than the second diameter of the distal portion 214 but less than the first diameter of the proximal portion 212 and the intermediate portion 216. In some embodiments, each of the diameters of the proximal portion 212, the distal portion 214, the intermediate portion 216, and the separation portion 218 may be constant along the length of the respective portion. In some embodiments, one or more, or all, of the diameters of the proximal portion 212, the distal portion 214, the intermediate portion 216, and the separation portion 218 may vary along the length of the respective portion of the shaft 210. In such instances, the above-mentioned diameter of the respective portion having a varying diameter may be a maximum diameter of the respective portion of the shaft 210.

The separation portion 218 may be configured to facilitate separation of the proximal portion 212 from the intermediate portion 216. In particular, the smaller diameter of the separation portion 218 may allow a user to separate the proximal portion 212 from the intermediate portion 216 (and the remainder of the swab 200) upon grasping the proximal portion 212 and the intermediate portion 216 and apply bending forces thereto until the separation portion 218 breaks. In this manner, after using the swab 200 to collect a sample, the separation portion 218 may be broken, the distal portion 214, the intermediate portion 216, and the tip portion 230 may be inserted into a transport vessel, such as a test tube, and the proximal portion 212 may be discarded. In some embodiments, the shaft 210 also may include a flange 220 extending outward from the proximal portion 212. The flange 220 may be positioned at or near the proximal end 202 of the swab 200. In this manner, the flange 220 may be configured to facilitate grasping and manipulation of the swab 200 by a user. Upon breaking the separation portion 218 of the swab 200, the flange 220 would be discarded along with the proximal portion 212.

Figure 2C:
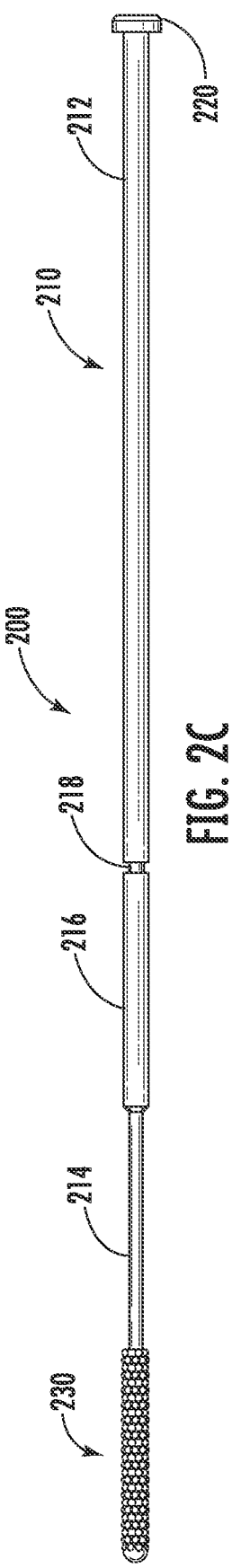
FIG. 2C is a front view of the three-dimensional printed swab of FIG. 2A.
Figure 2D:
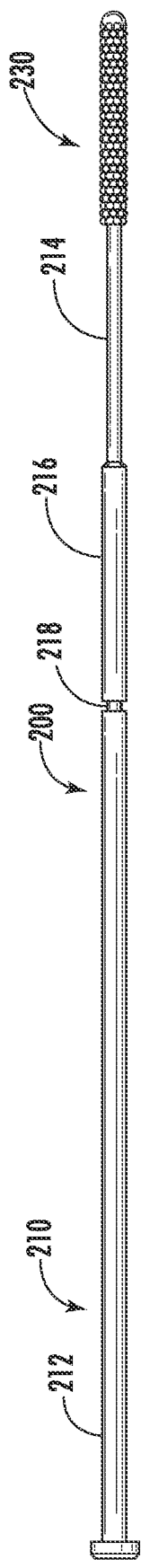
FIG. 2D is a rear view of the three-dimensional printed swab of FIG. 2A.
Figure 2E:
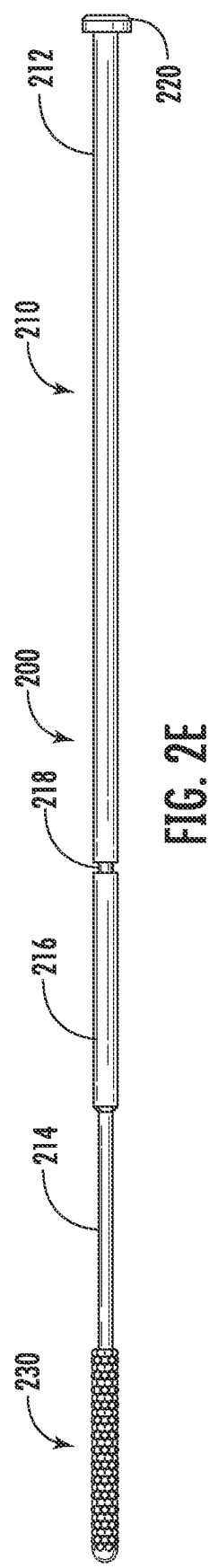
FIG. 2E is a top view of the three-dimensional printed swab of FIG. 2A.
Figure 2F:
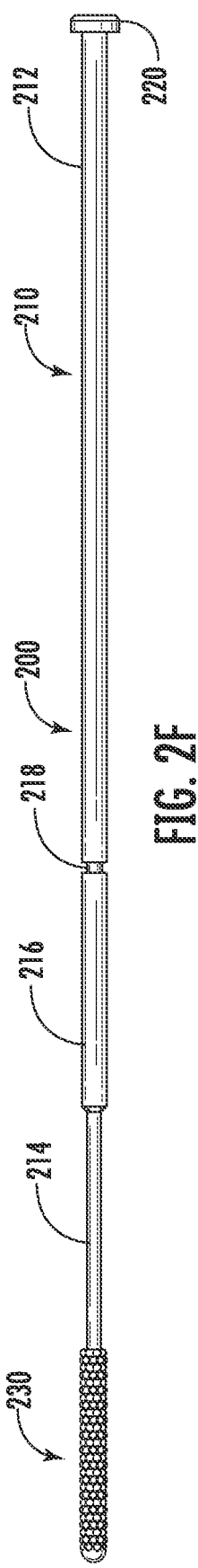
FIG. 2F is a bottom view of the three-dimensional printed swab of FIG. 2A.
Figure 2H:
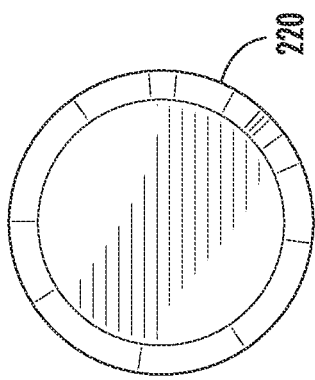
FIG. 2H is a detailed right-end view of the three-dimensional printed swab of FIG. 2A.
Figure 2G:
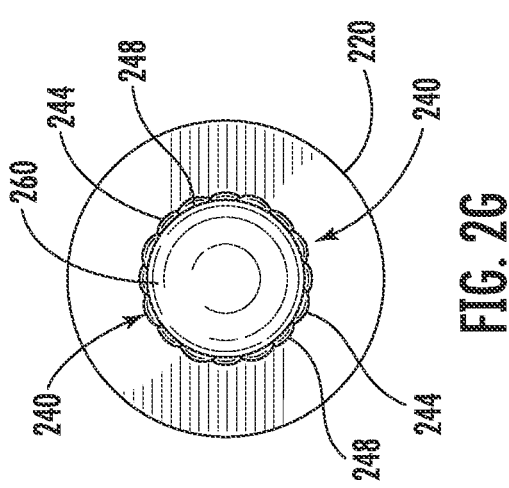
FIG. 2G is a detailed left-end view of the three-dimensional printed swab of FIG. 2A.
Figure 2I:
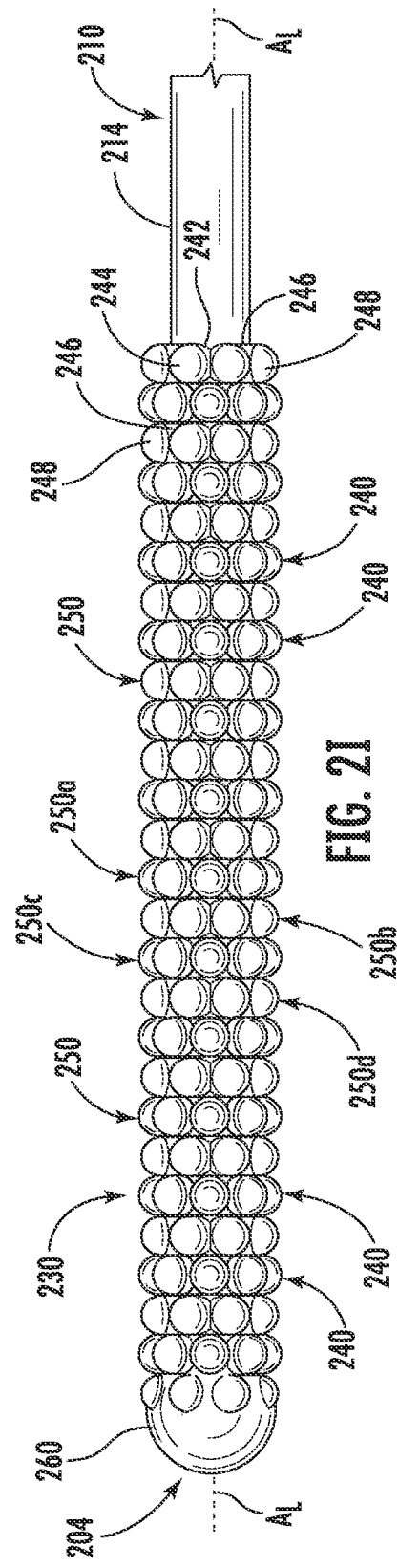
FIG. 2I is a detailed front view of the tip portion of the three-dimensional printed swab of FIG. 2A.

As shown, the tip portion 230 may include a plurality of protrusions 240 each extending outward from the shaft 210 and transverse to the longitudinal axis $A_L$ of the swab 200. The protrusions 240 may be configured to facilitate collection of a biological sample thereon. In some embodiments, as shown, the protrusions 240 may extend outward from the distal portion 214 of the shaft 210. In some embodiments, as shown, each of the protrusions 240 may extend perpendicular to the longitudinal axis $A_L$ of the swab 200. In other words, each of the protrusions 240 may extend in a radial direction relative to the longitudinal axis Az of the swab 200. Each of the protrusions 240 may have a base end 242 and a free end 244, with a distance between the base end 242 and the free end 244 defining a height (which alternatively may be referred to as a "length") of the protrusion 240. The free ends 244 may define a third diameter, as shown in FIG. 2G. In some embodiments, as shown, the third diameter may be greater than the first diameter of the proximal portion 212 and thus also greater than the second diameter of the distal portion 214. As compared to the protrusions 140 of the swab 100, the free ends 244 of the protrusions 240 of the swab 200 may define a smaller diameter more suitable for a pediatric human subject.

As shown, each of the protrusions 240 may include a protrusion base 246 and a protrusion tip 248. The protrusion base 246 may extend from the base end 242 to the protrusion tip 248, and the protrusion tip 248 may extend from the protrusion base 246 to the free end 244. In some embodiments, as shown, the protrusion base 246 may have a cylindrical shape, and the protrusion tip 248 may have a partial-spherical shape, such as a hemispherical same. Other shapes of the protrusion base 246 and the protrusion tip 248 may be used in other embodiments. In some embodiments, all of the protrusions 240 may have the same shape and the same size. In other embodiments, some of the protrusions 240 may have the same shape and the same size, while other protrusions 240 may have a different shape and/or a different size. For example, as shown in the illustrated embodiment, some of the protrusions 240 positioned at or near the distal end of the tip portion 230 may be smaller than the protrusions 240 positioned along an intermediate section of the tip portion 230 and may not include a cylindrical base.

As shown, the plurality of protrusions 240 may include a series of circumferential arrays 250 of the protrusions 240 positioned along the longitudinal axis $A_L$ of the swab 200. In some embodiments, the plurality of protrusions 240 may include four (4) or more circumferential arrays 250 positioned in series. Although twenty-seven (27) circumferential arrays 250 of the protrusions 240 are provided in the illustrated embodiment, fewer or more circumferential arrays 250 positioned in series may be used in other embodiments. In some embodiments, each of the circumferential arrays 250 may include four (4) or more protrusions 240 positioned in an array. Although eight (8) protrusions 240 are provided for each of the circumferential arrays 250 in the illustrated embodiment, fewer or more protrusions 240 for each of the circumferential arrays 250 may be used in other embodiments. In some embodiments, as shown, for each of the circumferential arrays 250, the respective free ends 244 of the protrusions 240 of the circumferential array 250 may be equally spaced apart from one another in the circumferential direction around the longitudinal axis $A_L$ of the swab 200. In some embodiments, for each of the circumferential arrays 250, the respective free ends 244 of the protrusions 240 of the circumferential array 250 may be spaced apart from one another at unequal distances in the circumferential direction. In some embodiments, as shown, for each or some of the circumferential arrays 250, the respective base ends 242 of consecutive pairs of the protrusions 240 of the circumferential array 250 may be positioned adjacent one another in the circumferential direction. In other words, the respective base ends 242 of consecutive pairs of the protrusions 240 may not be spaced apart from one another. In some embodiments, for each or some of the circumferential arrays 250, the respective base ends 242 of the protrusions 240 of the circumferential array 250 may be equally spaced apart from one another in the circumferential direction. In some embodiments, for each or some of the circumferential arrays 250, the respective base ends 242 of the protrusions 240 of the circumferential array 250 may be spaced apart from one another at unequal distances in the circumferential direction.

As shown, the series of circumferential arrays 250 of the protrusions 240 may include a first circumferential array 250*a*, a second circumferential array 250*b*, a third circumferential array 250*c*, and a fourth circumferential array 250*d* positioned consecutively along the longitudinal axis $A_L$ of the swab 200. In some embodiments, the respective protrusions 240 of each consecutive pair of circumferential arrays 250 may be offset from one another in the circumferential direction. For example, as shown, the protrusions 240 of the first circumferential array 250*a* may be offset from the protrusions 240 of the second circumferential array 250*b* in the circumferential direction, the protrusions 240 of the second circumferential array 250*b* may be offset from the protrusions 240 of the third circumferential array 250*c* in the circumferential direction, and the protrusions 240 of the third circumferential array 250*c* may be offset from the protrusions 240 of the fourth circumferential array 250*d* in the circumferential direction. In some embodiments, the respective protrusions 240 of each pair of circumferential arrays 250 separated from one another by only a single other circumferential array 250 may be aligned with one another in the circumferential direction. For example, as shown, the protrusions 240 of the first circumferential array 250*a* may be aligned with the protrusions 240 of the third circumferential array 250*c* in the circumferential direction, and the protrusions 240 of the second circumferential array 250*b* may be aligned with the protrusions 240 of the fourth circumferential array 250*d* in the circumferential direction.

In some embodiments, as shown, respective consecutive pairs of the circumferential arrays 250 may be positioned adjacent one another along the longitudinal axis $A_L$ of the swab 200. In other words, the respective base ends 242 of the protrusions 240 of consecutive pairs of the circumferential arrays 250 may not be spaced apart from one another along the longitudinal axis $A_L$ of the swab 200. In some embodiments, the circumferential arrays 250 may be positioned equally spaced apart from one another along the longitudinal axis $A_L$ of the swab 200. In some embodiments, the circumferential arrays 250 may be spaced apart from one another at unequal distances along the longitudinal axis $A_L$ of the swab 200. Various configurations of the series of circumferential arrays 250 may be used in different embodiments.

In some embodiments, the tip portion 230 also may include tip 260. As shown, the tip 260 may be positioned at the distal end of the tip portion 230 and may define the distal end 204 of the swab 200. The tip 260 may be configured to contact anatomical features and to guide the tip portion 230 to a target location of a subject during use of the swab 200. As shown, the tip 260 may include a rounded or otherwise curved surface for atraumatically contacting anatomical features of the subject. In some embodiments, as shown, the tip 260 may have a partial-spherical shape, although other shapes for the tip 260 may be used in other embodiments. In some embodiments, as shown, the protrusions 240 of one or more of the circumferential arrays 250 may extend outward from a portion of the tip 260, such as from a proximal half of the tip 260, while a distal half of the tip 260 may be devoid of any protrusions 240 extending therefrom. In some embodiments, the entire tip 260 may be devoid of any protrusions 240 extending therefrom. The tip 260 may have a fourth diameter, as shown in FIG. 2G. In some embodiments, as shown, the fourth diameter of the tip 260 may be less than the third diameter defined by the free ends 244 of the protrusions 240, greater than the first diameter of the proximal portion 212, and thus also greater than the second diameter of the distal portion 214. As compared to the tip 160 of the swab 100, the tip 260 of the swab 200 may define a smaller diameter more suitable for a pediatric human subject.

In some embodiments, the respective features of the three-dimensional printed swab 200 may have the relative dimensional relationships depicted in FIGS. 2A-2I. Such relative dimensional relationships may make the three-dimensional printed swab 200 particularly well suited for collecting biological samples from a pediatric human subject for diagnostic testing. Various other suitable relative dimensional relationships between respective features of the three-dimensional printed swab 200 may be used in other embodiments.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A three-dimensional printed swab comprising:
a shaft defining a longitudinal axis of the swab; and
a tip portion integrally formed with the shaft and defining an oblong shape, wherein the tip portion comprises a plurality of protrusions each extending outward from the shaft and transverse to the longitudinal axis to define a studded surface on the oblong tip portion,
wherein the tip portion further comprises a tip defining a distal end of the swab and having a partial-spherical shape, the tip being devoid of protrusions,
wherein the plurality of protrusions extending from the tip portion comprises a series of circumferential arrays of protrusions positioned along the longitudinal axis, and
wherein the series of circumferential arrays of protrusions comprises a first circumferential array of protrusions and a second circumferential array of protrusions positioned consecutively along the longitudinal axis, and wherein the protrusions of the first circumferential array of protrusions are offset from the protrusions of the second circumferential array of protrusions in the circumferential direction.

2. The three-dimensional printed swab of claim 1, wherein the series of circumferential arrays of protrusions further comprises a third circumferential array of protrusions positioned consecutively along the longitudinal axis with respect to the second circumferential array of protrusions, and wherein the protrusions of the first circumferential array of protrusions are aligned with the protrusions of the third circumferential array of protrusions in the circumferential direction.

3. The three-dimensional printed swab of claim 1, wherein the partial-spherical shape of the tip portion encompasses a portion of a sphere greater than a hemisphere.

4. The three-dimensional printed swab of claim 1, wherein each of the circumferential arrays of protrusions comprises four or more protrusions having respective free ends equally spaced apart from one another in a circumferential direction around the longitudinal axis.

5. The three-dimensional printed swab of claim 4, wherein the four or more protrusions have respective base ends equally spaced apart from one another in the circumferential direction.

6. The three-dimensional printed swab of claim 5, wherein the free ends of each of the four or more protrusions comprises a partial-spherical shape.

7. The three-dimensional printed swab of claim 4, wherein the series of circumferential arrays of protrusions includes a proximal circumferential array of protrusions disposed on a proximal end of the tip portion opposite from the distal end of the swab along the longitudinal axis,
wherein a diameter of the proximal circumferential array of protrusions is less than a diameter of any other one of the circumferential arrays of protrusions.

8. The three-dimensional printed swab of claim 1, wherein the circumferential arrays of protrusions are equally spaced apart from one another along the longitudinal axis.

9. The three-dimensional printed swab of claim 1, wherein each of the protrusions extends perpendicular to the longitudinal axis.

10. The three-dimensional printed swab of claim 1, wherein the shaft and the tip portion are formed of the same material.

11. A method for fabricating a three-dimensional printed swab, the method comprising:
receiving a digital three-dimensional model corresponding to the swab; and
integrally forming, via three-dimensional printing and based at least in part on the digital three-dimensional model, a shaft and a tip portion of the swab, wherein the shaft defines a longitudinal axis of the swab, wherein the tip portion defines an oblong shape, wherein the tip portion comprises a plurality of protrusions each extending outward from the shaft and transverse to the longitudinal axis to define a studded surface on the oblong tip portion,
wherein the tip portion further comprises a tip defining a distal end of the swab and having a partial-spherical shape, the tip being devoid of protrusions,
wherein the plurality of protrusions extending from the tip portion comprises a series of circumferential arrays of protrusions positioned along the longitudinal axis, and
wherein the series of circumferential arrays of protrusions comprises a first circumferential array of protrusions and a second circumferential array of protrusions positioned consecutively along the longitudinal axis, and wherein the protrusions of the first circumferential array of protrusions are offset from the protrusions of the second circumferential array of protrusions in the circumferential direction.

12. The method of claim 11, wherein each of the circumferential arrays of protrusions comprises four or more protrusions having respective free ends equally spaced apart from one another in a circumferential direction around the longitudinal axis.

13. The method of claim 11, wherein the shaft and the tip portion are formed of the same material.

* * * * *